(12) United States Patent
Johnson (10) Patent No.: US 7,675,622 B2
(45) Date of Patent: Mar. 9, 2010

(54) DETERMINING A MEDIA FEATURE USING A PHOTOVOLTAIC CELL AND AN ELECTROLUMINESCENT LIGHT PANEL

(75) Inventor: Jon R. Johnson, Vancouver, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 788 days.

(21) Appl. No.: 11/273,819

(22) Filed: Nov. 14, 2005

(65) Prior Publication Data

US 2007/0109538 A1 May 17, 2007

(51) Int. Cl.
*G01N 21/84* (2006.01)
(52) U.S. Cl. .................................... 356/429
(58) Field of Classification Search ............... 356/429; 399/389
See application file for complete search history.

(56) References Cited

U.S. PATENT DOCUMENTS

| | | | |
|---|---|---|---|
| 4,255,057 A * | 3/1981 | Williams | .................... 356/435 |
| 4,269,515 A * | 5/1981 | Altman | ....................... 356/394 |
| 4,723,072 A * | 2/1988 | Naruse | ....................... 235/454 |
| 4,778,272 A | 10/1988 | Asakura | |
| 4,960,336 A | 10/1990 | Brooks et al. | |
| 5,516,094 A | 5/1996 | Sander | |
| 5,796,472 A * | 8/1998 | Wirthlin | ...................... 356/72 |
| 5,991,046 A * | 11/1999 | Shakespeare et al. | ....... 356/429 |
| 6,130,438 A | 10/2000 | Torai | |
| 6,304,314 B1 * | 10/2001 | Rider et al. | ................... 355/27 |
| 6,323,948 B2 | 11/2001 | Haque et al. | |
| 6,386,676 B1 | 5/2002 | Yang et al. | |
| 6,459,494 B1 | 10/2002 | Kurokawa et al. | |
| 6,883,983 B2 | 4/2005 | Kobayashi | |
| 2005/0190368 A1 * | 9/2005 | Ehrhardt et al. | ............. 356/431 |

* cited by examiner

*Primary Examiner*—Tarifur Chowdhury
*Assistant Examiner*—Tara S Pajoohi (57) ABSTRACT

This invention relates to an apparatus for determining a media feature, comprising: a plurality of light filters such that the filters include a media measurement aperture and a calibration aperture and wherein the filters are spaced a predetermined distance apart to allow media to be introduced between the filters; a light source located substantially adjacent to one of the filters; and a light detector located substantially adjacent to another of the filters.

20 Claims, 12 Drawing Sheets

DETERMINING A MEDIA FEATURE USING A PHOTOVOLTAIC CELL AND AN ELECTROLUMINESCENT LIGHT PANEL

BACKGROUND OF THE INVENTION

1. Field of the Invention

This invention relates to an apparatus for determining a media feature, comprising: a plurality of light filters such that the filters include a media measurement aperture and a calibration aperture and wherein the filters are spaced a predetermined distance apart to allow media to be introduced between the filters; a light source located substantially adjacent to one of the filters; and a light detector located substantially adjacent to another of the filters.

2. Description of the Related Art

Prior to the present invention, as set forth in general terms above and more specifically below, it is known, that image forming devices are capable of printing images on media sheets of varying widths. Printing beyond the edges of a media sheet can cause a number of problems. It wastes imaging material such as ink and/or toner. The wasted imaging material can damage or decrease the life span of the image forming device. Also, the wasted imaging material can be inadvertently transferred to another media sheet thereby degrading print quality.

It is also known, that sensors can be employed to detect a variety of media and media defects. Such sensors include sensors attached to moving carriages that scan across the media and fixed/stationary sensors. While these sensors are capable of detecting a variety of media and media defects, these sensors either require time to move which results in coordination complexity and loss of throughput (time lost while moving the sensor) or relatively small sensors that are expensive and may not provide enough resolution. Finally, none of these sensors detect media features, such as tabs and are self-calibrating.

It is apparent from the above that there exists a need in the art for a media sensing device which is capable of detecting media, media defects, and media features, such as tabs, but which at the same time is self-calibrating. It is a purpose of this invention to fulfill this and other needs in the art in a manner more apparent to the skilled artisan once given the following disclosure.

SUMMARY OF THE INVENTION

Generally speaking, an embodiment of this invention fulfills these needs by providing an apparatus for determining a media feature, comprising: a plurality of light filters such that the filters include a media measurement aperture and a calibration aperture and wherein the filters are spaced a predetermined distance apart to allow media to be introduced between the filters; a light source located substantially adjacent to one of the filters; and a light detector located substantially adjacent to another of the filters.

In certain preferred embodiments, the media measurement aperture and calibration aperture of each of the filters are in alignment with each other. Also, the light source is comprised of a uniform light source, such as an electroluminescent panel. Finally, the light detector is comprised of a photovoltaic cell.

In another further preferred embodiment, the apparatus for determining a media feature is capable of detecting media, media defects, and media features, such as tabs, but which at the same time is self-calibrating.

The preferred apparatus for determining a media feature, according to various embodiments of the present invention, offers the following advantages: ease-of-use; ease of detecting media; ease of detecting media defects; and ease of detecting media features. In fact, in many of the preferred embodiments, these factors of ease of detecting media, ease of detecting media defects, and ease of detecting media features are optimized to an extent that is considerably higher than heretofore achieved in prior, known apparatus for determining media features.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

INTRODUCTION: A given image forming device can be capable of printing on media having varying features. Examples of features include width as well as the presence and location of holes and tabs, and defects such as tears. To extend the life of the device, help reduce waste of imaging material such a toner or ink, and to help achieve a desired level of print quality, the image forming device may be made aware of the features of the media on which it is about to print. Various embodiments function to identify the width and other features of a sheet of print media.

The following description is broken into sections. The first section, labeled "components," describes an example of the physical and logical components of an image forming device in which various embodiments of the invention may be implemented. The second section, labeled "Media Width" describes an exemplary series of method steps and examples for detecting the width of a sheet of print media. The third section, labeled "Identifying Holes" describes an exemplary series of method steps and examples for detecting the presence of a hole in a sheet of print media. The fourth section, labeled "Locating Holes," describes an exemplary series of method steps and examples for identifying the location and size of a hole in a sheet of print media. The fifth section, labeled "Locating Tabs," describes an exemplary series of method steps and examples for identifying the location and size of media tabs.

Figure 1:
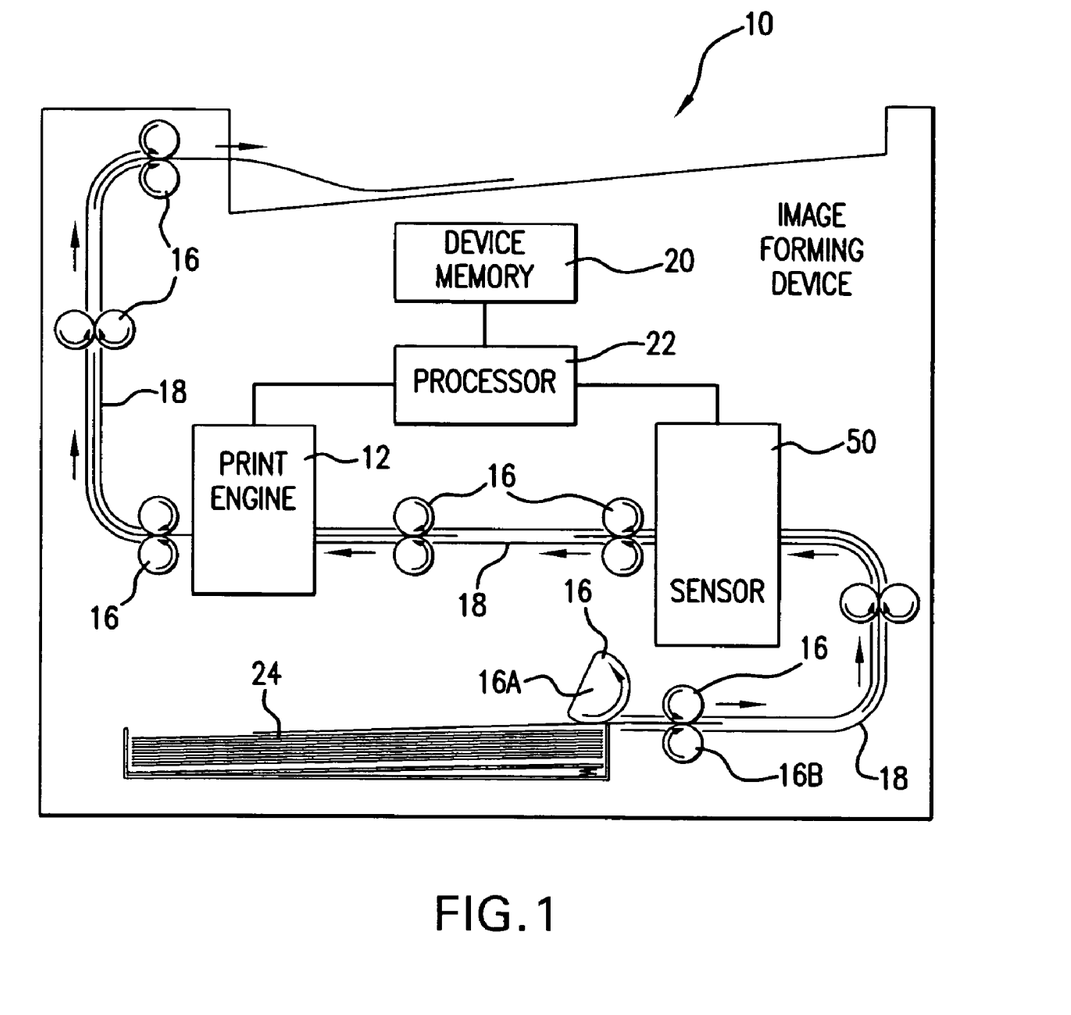
FIG. 1 is a block diagram of an exemplary image forming device in which various embodiments of the present invention may be implemented.

COMPONENTS: FIG. 1 illustrates an exemplary image forming device 10 in which various embodiments of the present invention may be implemented. Image forming device 10 represents generally any device capable of forming an image on a sheet of paper or other print media. Image forming device 10 includes print engine 12, sensor 50, media drive 16, media path 18, device memory 20, and processor 22.

Print engine 12 represents generally the hardware components capable of forming an image on print media. Where, for example, image forming device 10 is a laser printer, print engine 12 may include a laser, a fuser, and a toner cartridge housing a toner reservoir, a photoconductive drum, a charging device, and a developer. In operation, the charging device places a uniform electrostatic charge on a photoconductive drum. Light from the laser is scanned across the photoconductive drum in a pattern of a desired print image. Where exposed to the light, the photoconductive drum is discharged creating an electrostatic version of the desired print image. The developer transfers charged toner particles from the toner reservoir to the photoconductive drum. The charged toner particles are repelled by the charged portions of the photoconductive drum but adhere to the discharged portions. The charge roller charges or discharges the print media sheet. As the media sheet passes across the photoconductive drum, toner particles are then transferred from the photoconductive drum to the media sheet. The fuser thermally fixes the transferred toner particles to the media sheet.

Where, for example, image forming device 10 is an ink printer, print engine 12 might include a carriage and an ink cartridge housing an ink reservoir and one or more print heads. In operation, the print heads selectively eject ink from the ink reservoir onto a media sheet, according to a desired print image. The carriage selectively moves and positions the print head relative to a media sheet such that the ejected ink forms the desired print image.

Figure 2:
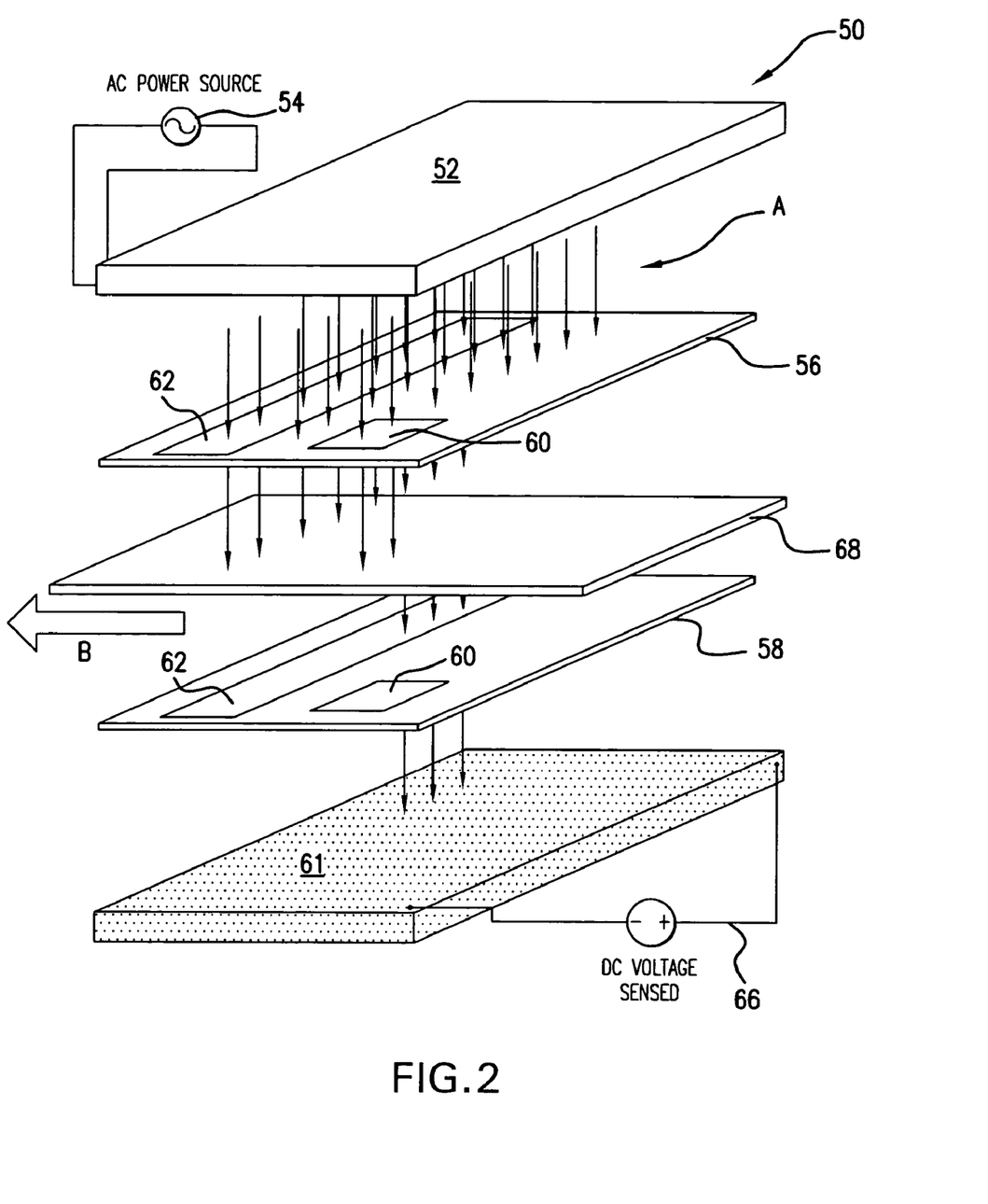
FIG. 2 is a schematic illustration of an apparatus for determining a media feature, according to one embodiment.

Sensor 50, described in more detail below with reference FIG. 2, represents hardware components capable of being used to identify one or more print media features by detecting the change in voltage level resulting from a change in light detected by the photovoltaic cell as the media passes through sensor 50. Media drive 16 represents the hardware components capable of urging print media along media path 18. Media path 18 represents generally the path along which print media flow through image forming device 10 during a printing operation.

Device memory 20 represents generally any computer readable medium or media capable of storing programs and data for controlling the operation of print engine 12, sensor 50, and media drive 16. Examples of programs stored by device memory 20 are described below with reference to FIG. 3. Processor 22 represents generally any processor capable of executing programs contained in device memory 20.

As shown, media drive 16 includes pick roller 16A and pinch rollers 16B. Pick roller 16A is responsible for selectively feeding print media from media source 24 into media path 18. Pinch rollers 16B are responsible for urging print media along media path 18 past sensor 50 and print engine 12. As shown, sensor 50 is located upstream from print engine 12 along media path 18. In this manner sensor 50 can be used to identify a print media feature and then the operation of print engine 12 can be directed, according to the identified feature. For example, where the feature is a width of the print media, print engine 12 can be directed not to print beyond the edges of the print media.

With respect to FIG. 2, FIG. 2 illustrates sensor 50. Sensor 50 includes, in part, uniform light source 52, conventional AC power source 54, a plurality of light filters 56, 58, a calibration aperture 60 located in each of the light filters 56, 58, a media measurement aperture 62 located in each of the light filters 56, 58, a light detector 61 which detects a sensed DC voltage 66, and a media 68. Preferably, the uniform light source 52 includes, but is not limited to, an electroluminescent panel. Also, the light detector 61 includes, but is not limited to, a photovoltaic cell. Detector 61 is used to measure the change in light brightness and creates a change in the emitted voltage level as the light brightness changes.

As shown in FIG. 2, light source 52 is located opposite light detector 61. As different sizes of media 68 pass (in the direction of arrow B) between light filters 56 and 58, different amounts of light arrive at light detector 61 (along the directions of arrows A) thereby creating a corresponding and proportional DC voltage. It is to be understood that larger media 68 will block more light and produce a lesser DC voltage than smaller media 68.

Filters 56 and 58 with matching apertures 60 and 62 are used to calibrate and measure the media 68 as media 68 passes between filters 56 and 58. Calibration aperture 60 is located in the media path so that it is always blocked by media 68 (before media 68 arrives at measurement aperture 62) regardless of the dimensions of media 68. This allows sensor 50 to measure the translucence of the media and use it with the measurement aperture 62. The leading edge of the media 68 first passes across the calibration aperture 60 and a translucence factor is computed based on the voltage measured at that moment and the known size of the calibration aperture 60. Next, as the leading edge of media 68 passes through measurement aperture 62 (different sizes of media will block more or less of the measurement aperture 62), the actual size of the media 68 is computed based on the voltage measured and the previously computed calibration factor. Precise positioning control of media 68, as it is transported through sensor 50, allows for straightforward sampling times to measure the DC voltage by light detector 61. It is to be understood that multiple configurations are possible. For example, some printing devices will justify the media to one side, thereby requiring only one sensor 50. For center justified media, two sensors 50 would likely be needed to simultaneously observe both edges of the media 68.

Figure 3:
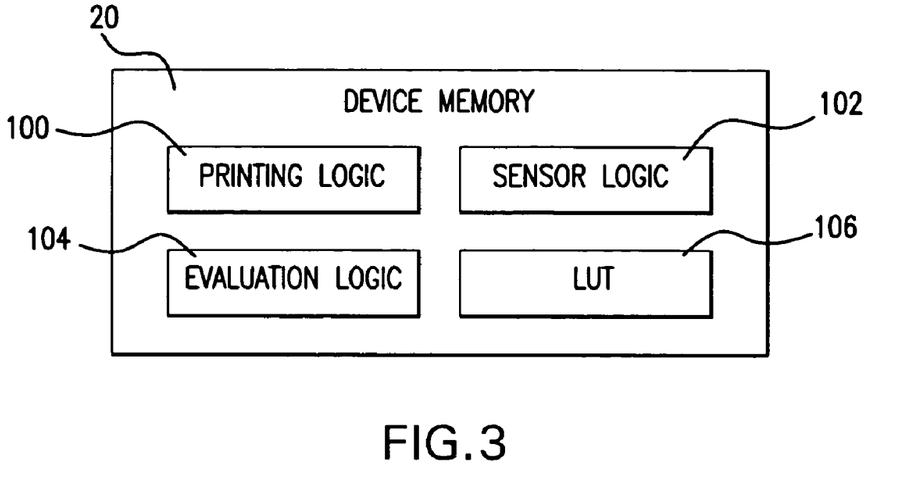
FIG. 3 is an exemplary block diagram illustrating the logical program elements for implementing various embodiments of the present invention.

Turning now to FIG. 3, device memory 20 includes printing logic 100, sensor logic 102, evaluation logic 104, and LUT (Look Up Table) 106. Printing logic 100 represents generally any program or programs capable of directing media drive 16 (FIG. 1) to urge a print media sheet along paper path 18 past print engine 12 as well as any program or programs capable of directing print engine 12 to form or to not form a desired image on the print media.

Sensor logic 102 represents generally any program or programs capable of collecting voltage level change data from sensor 50 (FIG. 1). At discrete points in time, sensor 50 generates a signal corresponding to a measured change in voltage level. The value of the signal at each point in time is referred to as voltage level data. Also, a series of such values obtained over a time period is also referred to as voltage level change data.

Evaluation logic 104 represents generally any program or programs capable of analyzing voltage level change data to identify a print media feature. Examples of such features include print media width, the presence of a hole, the size and location of a hole, and media extensions, such as tabs. When performing its function, evaluation logic 104 may access and use data contained in LUT 106. For example, evaluation logic 104 may access an entry in LUT 106 that corresponds to voltage level change data collected by sensor logic 102. That entry might then contain data identifying a print media feature or data to be used to calculate the print media feature.

Figure 4:
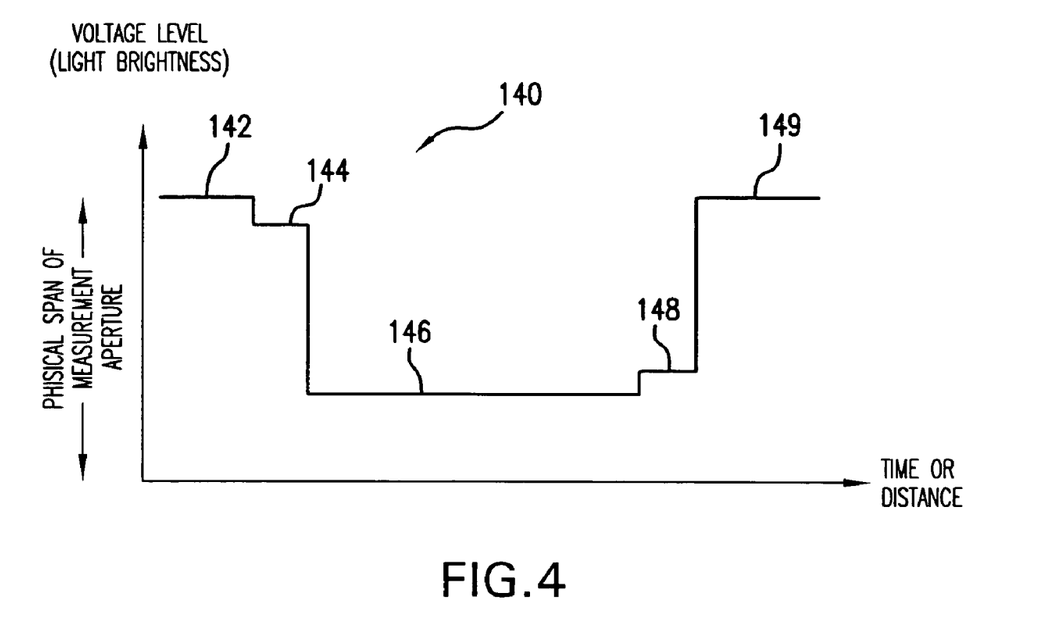
FIG. 4 is an exemplary two-dimensional graph charting voltage level change as a media sheet with no holes passes a sensor, according to an embodiment of the present invention.
Figure 5:
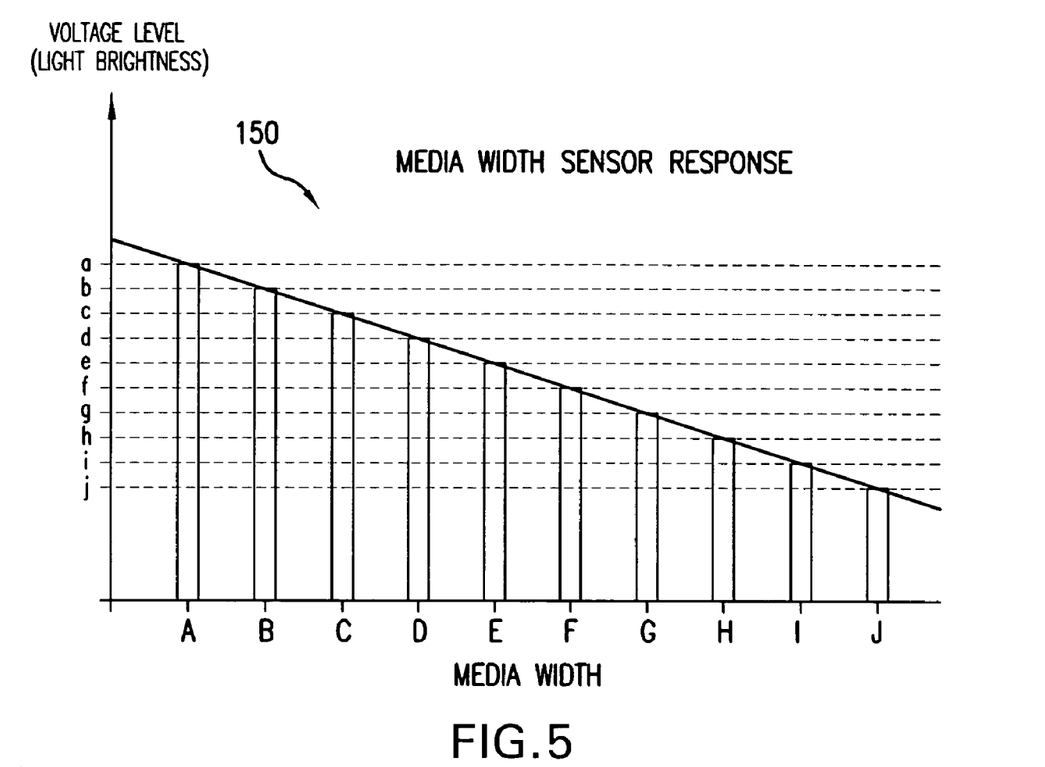
FIG. 5 is an exemplary chart illustrating how detected voltage level can vary based on media width, according to an embodiment of the present invention.
Figure 6:
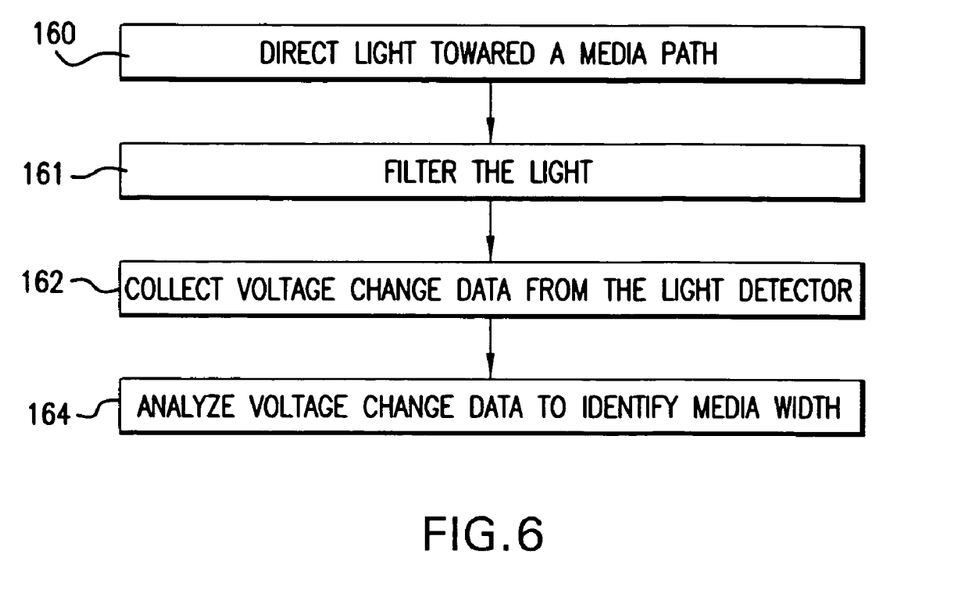
FIG. 6 is an exemplary flow diagram illustrating steps taken to identify a media width, according to an embodiment of the present invention.

MEDIA WIDTH: FIG. 4-6 helps illustrate a method for identifying a media width based on a change in voltage level measured by sensor 50 (FIG. 1). FIG. 4 is a two-dimensional graph 140 illustrating a measured voltage level as a media sheet passes through sensor 50. Initially, the measured voltage level is at a relatively high value 142. When a leading edge of the media sheet enters calibration aperture 60, the measured voltage level drops to a lower value 144. When the leading edge enters measurement aperture 62, the measured voltage level drops to a relatively low value 146. When the trailing edge of media enters the calibration aperture 60, the measured voltage level rises to a higher value 148. Once the trailing edge enters the measurement aperture 62, the measured voltage level returns to a relatively high value 149. The width of the print media can be calculated as a function of the measured voltage level change. The presence of relatively low level 146 indicates a media width of a discernable value.

Media width sensor chart 150 of FIG. 5 helps illustrate how detected light intensity can vary based on media width. LUT 106 (FIG. 3) may include ten entries identifying different media widths A-J. Each entry can be identified by data corresponding to a different voltage level value. For example, the entry identifying media width (A) can be identified by data corresponding to voltage level change value (a) and so on. When voltage level data collected by sensor logic 102 indicates a change in measured voltage level from a relatively high value to a relatively low value, the voltage level data corresponding to that relatively low value can be used by evaluation logic 104 to access an entry in LUT 106 that identifies a media width.

FIG. 6 is an exemplary flow diagram illustrating method steps for identifying print media width. Light is directed toward a media path (step 160). The light beam is directed from a first side of the media path such that the beam spans at least a portion of a width of a media path. The light is filtered prior to converging on a light detector (step 161). Voltage change data is collected from the light detector (step 162). The voltage change data collected corresponds to a voltage change measured from a second side of the media path opposite the first side as print media is urged along the media path. The voltage change data is analyzed to identify a width of the print media (step 164).

Figure 7:
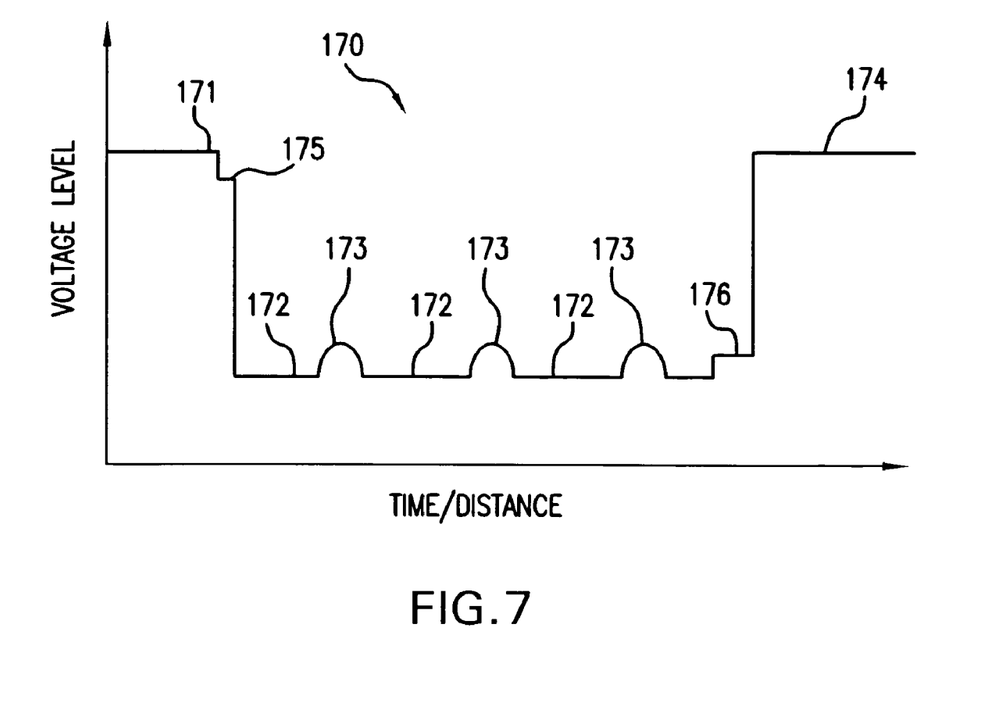
FIG. 7 is an exemplary two-dimensional graph charting voltage level as a media sheet with three holes passes a sensor, according to an embodiment of the present invention.

IDENTIFYING HOLES: FIG. 7-10 help illustrate a method for identifying holes in print media based on collected voltage change data. FIG. 7 is a two-dimensional graph 170 illustrating a measured voltage level as a media sheet with three holes passes through sensor 50 (FIG. 1). Initially, the measured voltage level is at a relatively high value 171. When a leading edge of the media sheet enters the calibration aperture 60, the measured voltage level drops to a lower value 175. When a leading edge of a media sheet enters measurement aperture 62, the measured voltage level drops to a relatively low value 172. Voltage changes 173 correspond to the three holes. As a segment of the media sheet with a hole enters, passes through, and then exits sensor 50, the measured voltage increases and then decreases back to the relatively low value 172. When the trailing edge of media enters the calibration aperture 60, the measured voltage level rises to a higher value 176. Once the trailing edge exits calibration sensor 62, the measured intensity returns to a relatively high value 174.

The existence of a hole can be identified by noting a first change in voltage from the relatively high value 171 to the relatively low value 172 and then a second change in which the measured voltage increases to a value less than the relatively high value and returns to the relatively low value. Analyzing the second change can reveal whether or not the second change resulted from a hole rather than a tear or other defect. Voltage change graph 180 of FIG. 8 helps illustrate.

Figure 8:
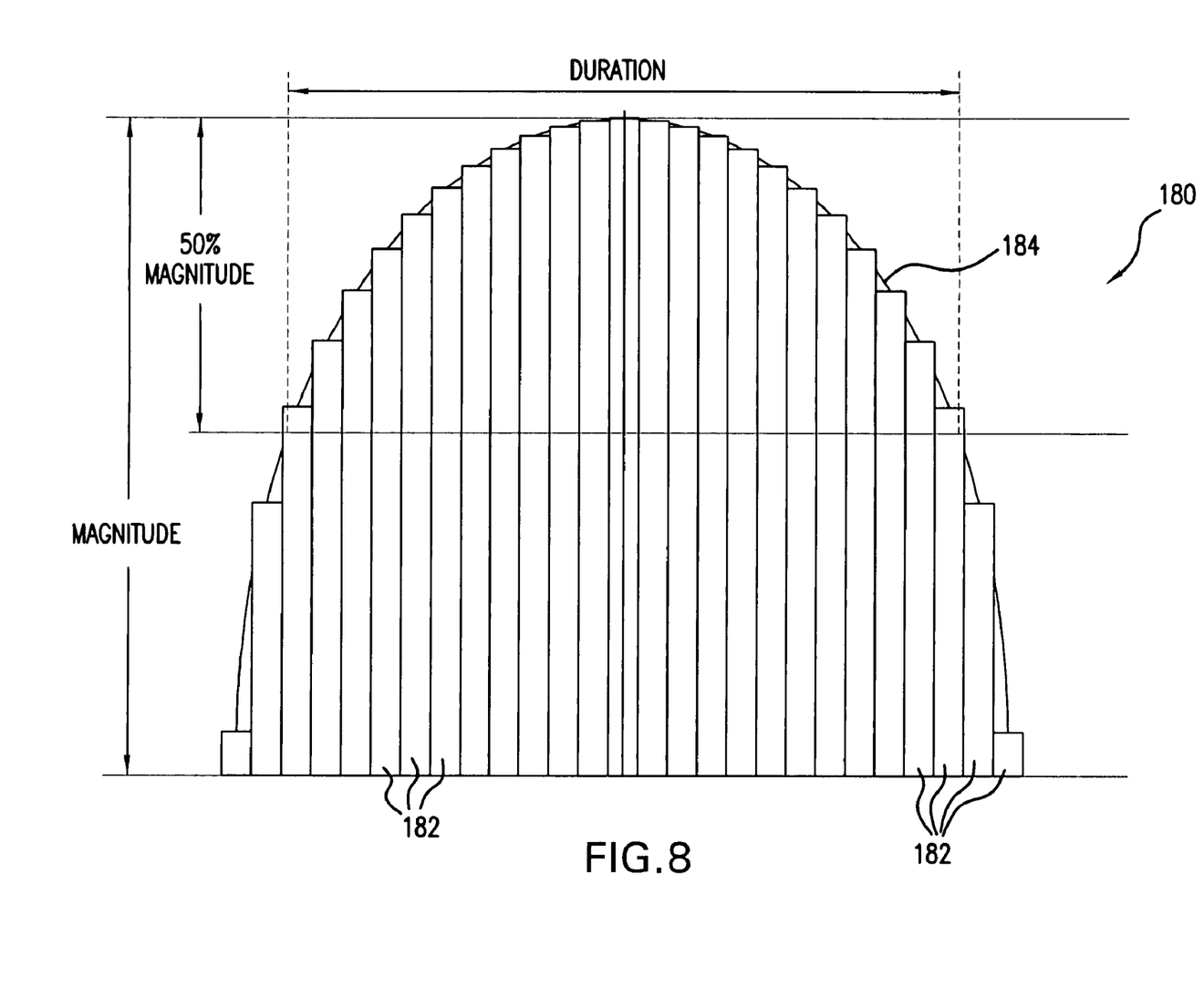
FIG. 8 is an exemplary two dimensional graph charting a change in voltage level caused by a hole, according to an embodiment of the present invention.

Graph 180 charts a change in measured voltage resulting from a hole. Chart 180 includes a series of segments 182 each corresponding to a measured voltage at a given point in time. A curve 184 is defined by a series of points representative of the voltage change indicated by each segment 182 as a function of time. Curve 184 has a magnitude and a duration, as indicated in FIG. 8. The indicated duration is the duration for which the voltage change is equal to or greater than fifty percent of the magnitude. A suspected diameter can be determined based on the magnitude—a particular magnitude indicates a corresponding diameter. Using the velocity at which the print media travels through sensor 50 (FIG. 1), a width corresponding to the indicated duration can be calculated. The cause of the voltage change represented by curve 184 can then be confirmed to be a hole if that width equals approximately eighty-six percent of the suspected diameter.

Figure 9:
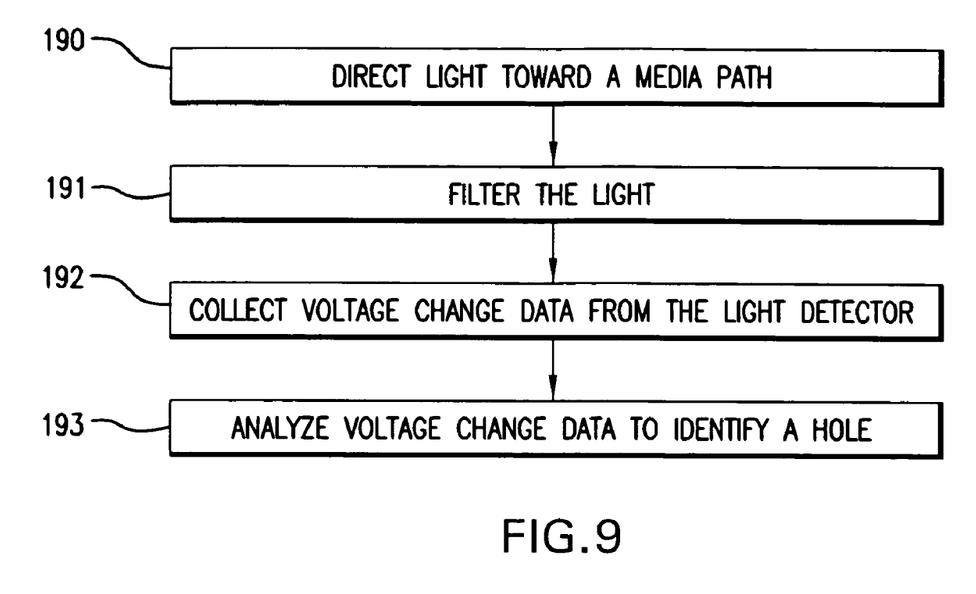
FIG. 9 is an exemplary flow diagram illustrating steps taken to identify a hole, according to an embodiment of the present invention.

FIG. 9 is an exemplary flow diagram illustrating method steps for identifying a hole. Light beam is directed toward a media path (step 190). The light beam is directed from a first side of the media path such that the beam spans at least a portion of a width of a media path. The light is filtered and then impinges upon a light detector (step 191). Voltage change data is collected from the light detector (step 192). The voltage change data collected corresponds to a voltage change measured from a second side of the media path opposite the first side as print media is urged along the media path. The voltage change data is analyzed to identify the presence of a hole (step 193).

Figure 10:
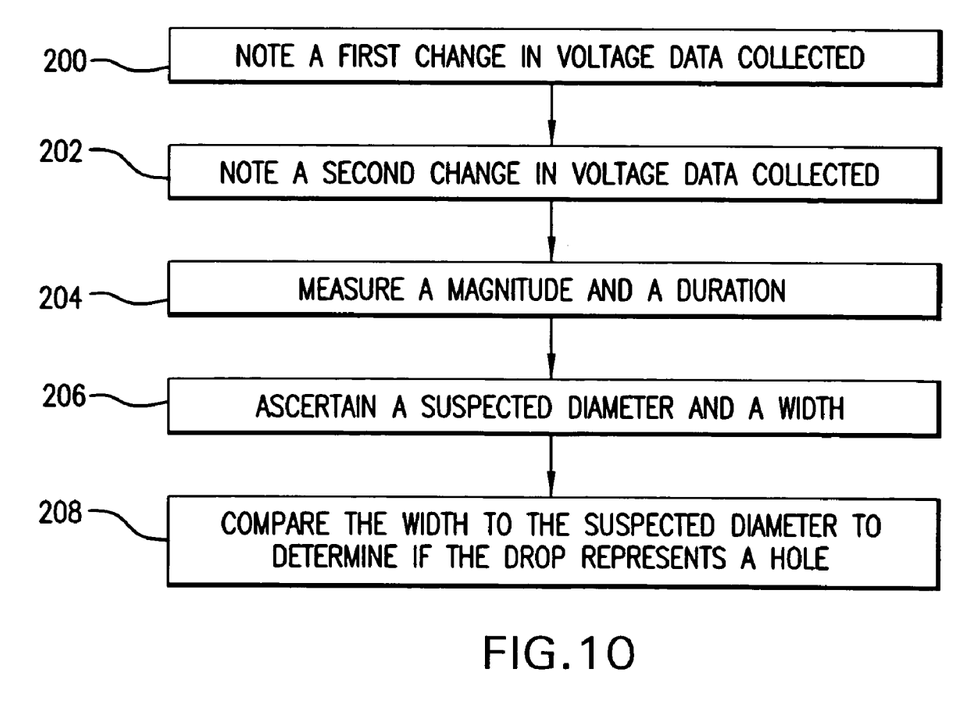
FIG. 10 is an exemplary flow diagram illustrating steps taken to determine if a change in voltage level data represents a hole, according to an embodiment of the present invention.

FIG. 10 is an exemplary flow diagram expanding on step 193. A first change in voltage data collected is noted (step 200). The first change, for example, may be a change from a relatively high value to a relatively low value indicating that the leading edge of a media sheet has been detected. A second change in the collected voltage data is then noted (step 202). The second, change, for example, may be an increase from the relatively low value to a value less than the relatively high value. The magnitude of the second change and a duration for which the second change is equal to or greater than fifty percent of the magnitude measured (step 204). A suspected diameter corresponding to the magnitude and a width corresponding to the duration are ascertained (step 206). The suspected diameter and the width are compared to determine if the second change was caused by a hole (step 208). Where the width is approximately equal to eight-six percent of the suspected diameter, it can be presumed that the second change was caused by a hole.

Figure 11:
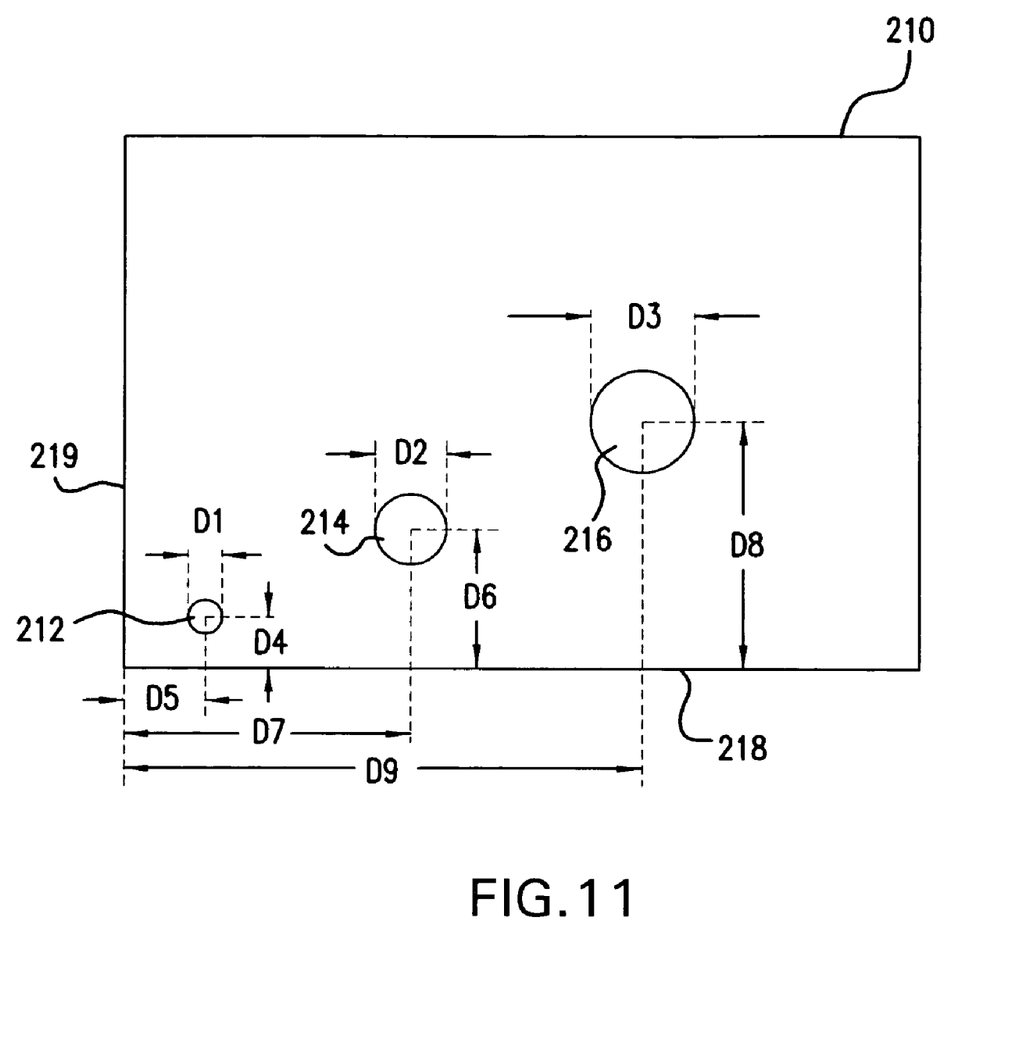
FIG. 11 illustrates an exemplary media sheet having variously placed and sized holes.

LOCATING HOLES: FIG. 11-14 help illustrate a method for locating holes in print media based on collected voltage change data. FIG. 11 illustrates media sheet 210 having variously sized and located holes 212-216. Hole 212 has a diameter D1. Hole 214 has a diameter D2, and hole 216 has a diameter D3. Measured from its center, hole 212 has a side edge distance D4 (distance from side edge 219) and is located a distance D5 from leading edge 219. Hole 214 has a side edge distance D6 and is located a distance D7 from leading edge 219. Hole 216 has a side edge distance D8 and is located a distance D9 from leading edge 219.

Figure 12:
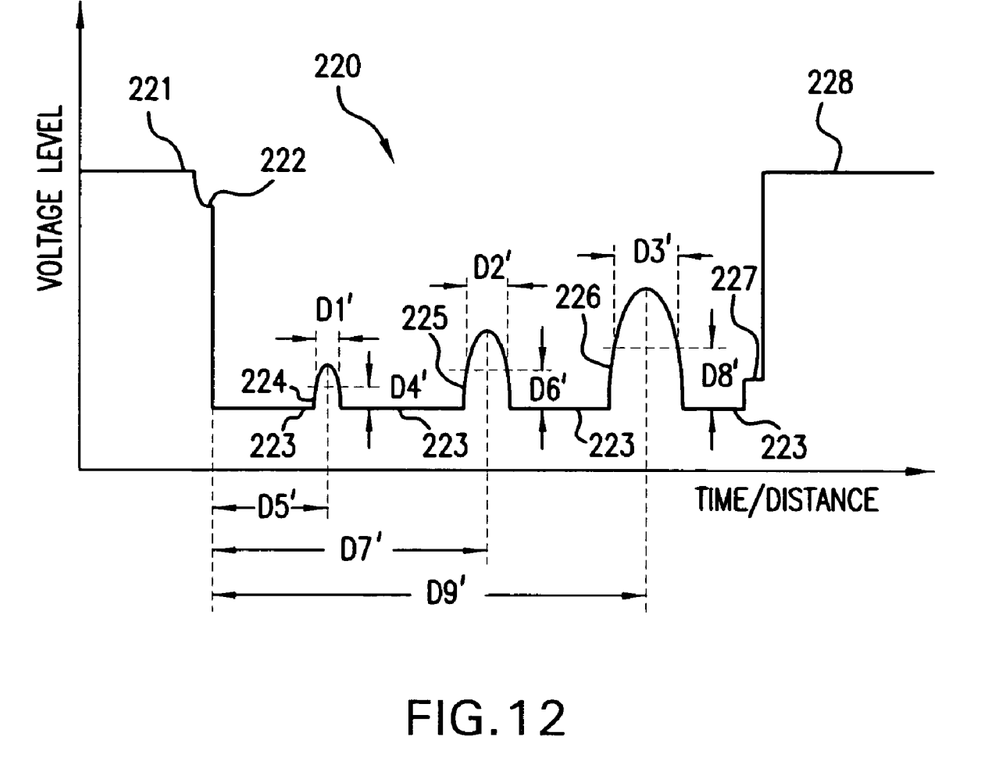
FIG. 12 is an exemplary two dimensional graph charting a change in voltage level caused by variously placed and sized holes as the media sheet of FIG. 11 passes between the apparatus of FIG. 2, according to an embodiment of the present invention.

FIG. 12 is a two-dimensional graph 220 illustrating a measured voltage level as a media sheet 210 (FIG. 11) with three variously sized and located holes passes through sensor 50 (FIG. 1). Initially, the measured voltage level is at a relatively high value 221. When a leading edge of the media sheet enters the calibration aperture 60, the measured voltage level drops to a lower value 222. When a leading edge of a media sheet 94 enters measurement aperture 62, the measured intensity level drops to a relatively low value 223. Voltage level change 224 corresponds to hole 212 (FIG. 11). Voltage level change 225 corresponds to hole 214 (FIG. 11), and voltage level change 226 corresponds to hole 216 (FIG. 11). When the trailing edge of the media 210 enters the calibration aperture 60, the measured voltage level rises to a higher value 227. Once the trailing edge exits sensor 50 (FIG. 1), the measured intensity returns to a relatively high value 228.

Focusing on FIG. 12, voltage level change 224 has dimensions D4', D1' and D5'. D4' corresponds to fifty percent of its magnitude. D1' corresponds to its width at the fifty-percent magnitude level. D5' corresponds to the time between when the leading edge of the media sheet entered measurement aperture 62 and when voltage level change 224 reached its peak magnitude.

Referring back to FIG. 11, side edge distance D4 can be calculated as a function of D4' (FIG. 12). The two will vary by a linear factor that depends primarily on the known size of calibration filter 60 (FIG. 1) and the measured change in voltage level.

Where the velocity of media sheet 94 is known, D1' and D5' can be converted to linear distances D1" and D5". Referring to FIG. 11, hole diameter D1 can be calculated as a function of D1". D1" equals approximately eighty-six percent of D1. Leading edge distance D5 then equals D5".

Focusing again on FIG. 12, intensity change 114 has dimensions D2', D6' and D7'. D6' corresponds to fifty percent of its magnitude. D2' corresponds to its width at the fifty-percent magnitude level. D7' corresponds to the time between when the leading edge of the media sheet entered sensor 14' and when intensity change 114 reached its peak magnitude.

Referring back to FIG. 11, side edge distance D6 can be calculated as a function of D6' (FIG. 19). The two will vary by a linear factor that depends primarily on the known size of calibration aperture 60 (FIG. 1) and the measured change in voltage level.

Where the velocity of media sheet 210 is known, D2' and D7' can be converted to linear distances D2" and D7." Referring to FIG. 11, hole diameter D2 can be calculated as a function of D2". D2" equals approximately eighty-six percent of D2. Leading edge distance D7 then equals D7".

Focusing once again on FIGS. 11 and 12, voltage level change 226 has dimensions D8', D3' and D9'. D8' corresponds to fifty percent of its magnitude. D3' corresponds to its width at the fifty-percent magnitude level. D9' corresponds to the time between when the leading edge of the media sheet entered measurement aperture 62 and when the voltage level change 226 reached its peak magnitude.

Referring back to FIG. 11, side edge distance D8 can be calculated as a function of D8' (FIG. 12). The two will vary by a linear factor that depends primarily on the known size of the calibration aperture 60 (FIG. 1) and the measured change in voltage level.

Where the velocity of media sheet 210 is known, D3' and D9' can be converted to linear distances D3" and D9". Referring to FIG. 11, hole diameter D3 can be calculated as a function of D3". D3" equals approximately eighty-six percent of D3. Leading edge distance D9 then equals D9".

Figure 13:
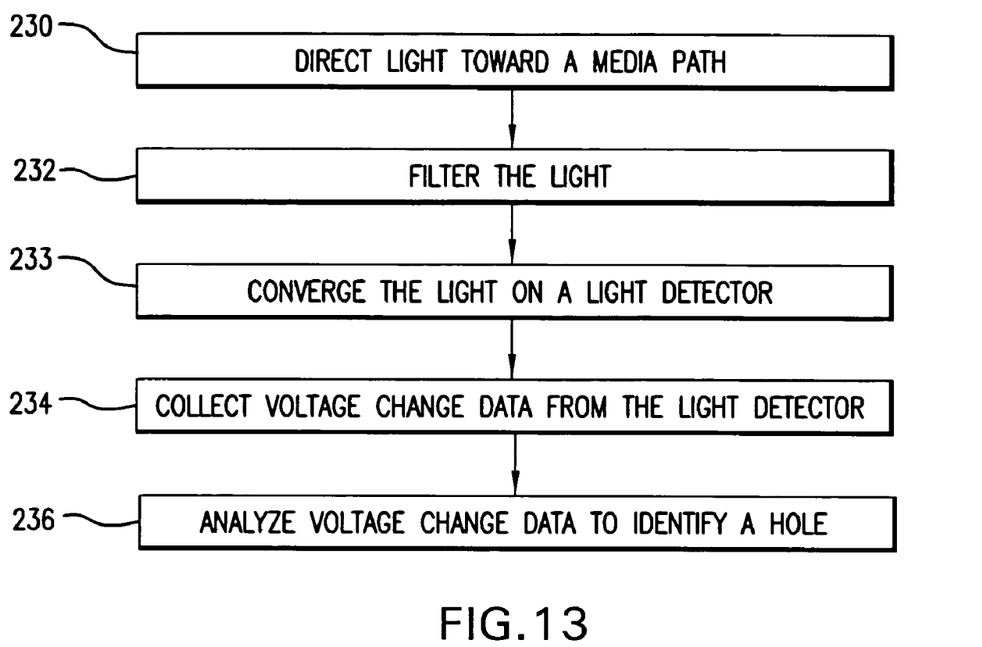
FIG. 13 is an exemplary flow diagram illustrating steps taken to locate a hole, according to an embodiment of the present invention.

Moving on, FIG. 13 is an exemplary flow diagram illustrating method steps for locating a hole. Light is directed toward a media path (step 230). The light is directed from a first side of a media path such that the light spans at least a portion of a width of the media path. The light is filtered (step 232). The light impinges upon a light detector (step 233). Voltage level change data is collected from the light detector (step 234). The voltage level change data collected corresponds to a voltage level change measured from a second side of the media path opposite the first side as print media is urged along the media path. The voltage level change data is analyzed to locate a hole (step 236).

Figure 14:
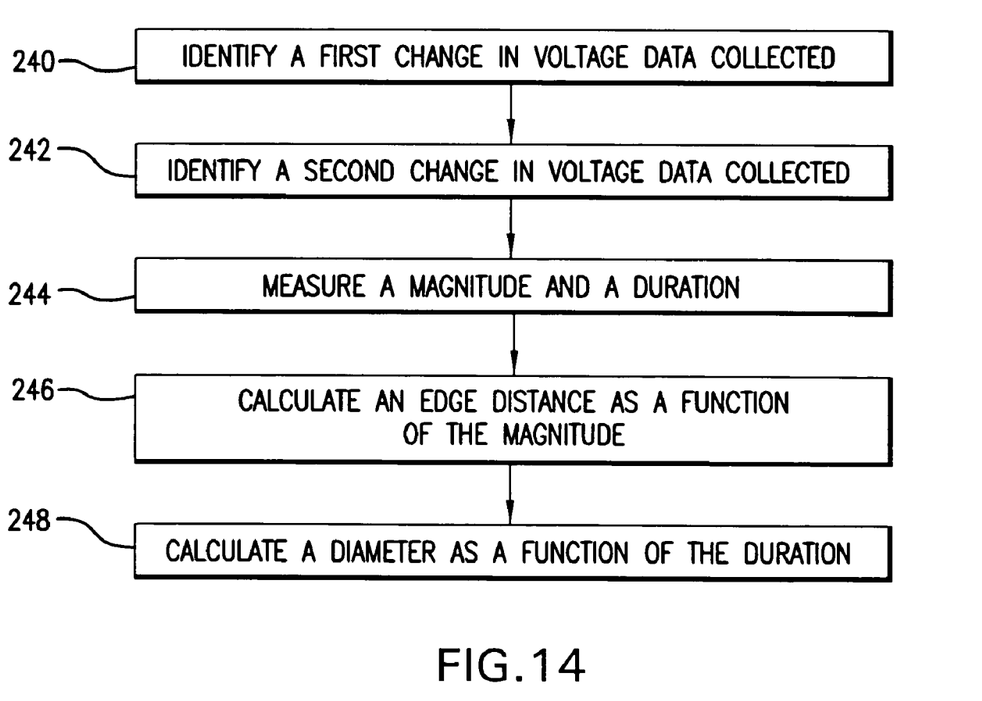
FIG. 14 is an exemplary flow diagram illustrating steps taken to identify a location and size of a hole based on a change in voltage level caused by that hole, according to an embodiment of the present invention.

FIG. 14 is an exemplary flow diagram expanding on step 236. A first change in voltage data collected is noted (step 240). The first change, for example, may be a change from a relatively high value to a relatively low value indicating that the leading edge of a media sheet has been detected. A second change in the collected voltage level data is then noted (step 242). The second change, for example, may be an increase from the relatively low value to a value less than the relatively high value and then a return to the relatively low value. The magnitude of the second change and a duration of the second change at fifty percent of its magnitude are measured (step 244). An edge distance is calculated as a function of the measured magnitude (step 246). A diameter is calculated as a function of the measured duration (step 248).

Figure 15:
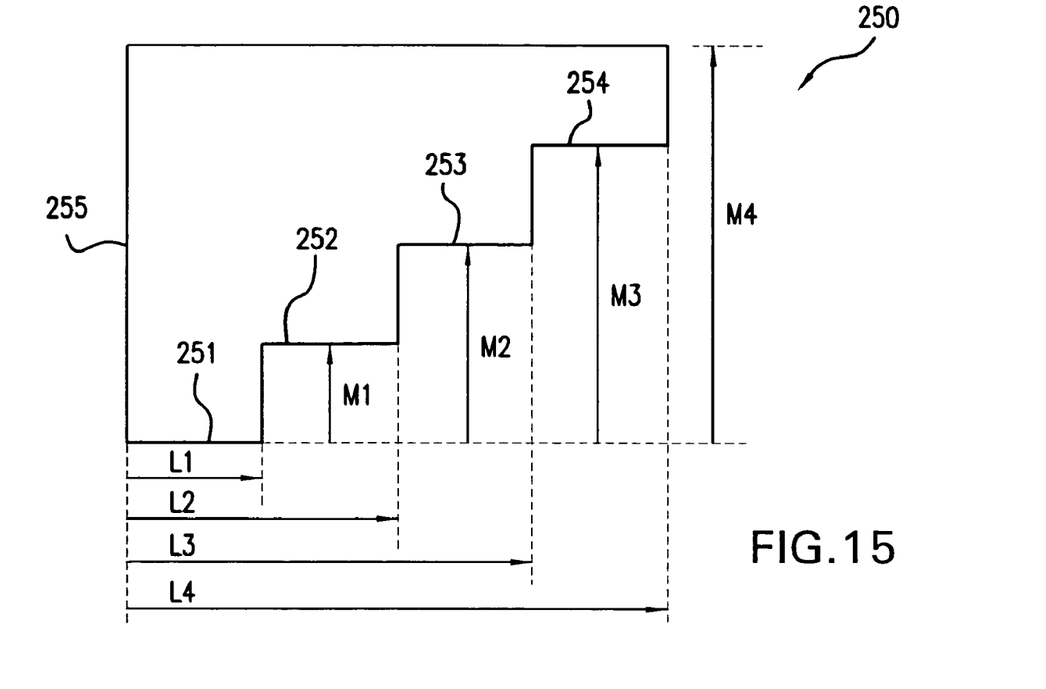
FIG. 15 illustrates an exemplary media sheet having variously placed and sized tabs.

Locating Tabs: FIG. 15-18 help illustrate a method for locating holes in print media based on collected voltage change data. FIG. 15 illustrates media sheet 250 having variously sized and located tabs 251-254. Tab 251 has a length L1. Tab 252 has a length L2. Tab 253 has a length L3. Tab 253 has a length L4. Measured from length L1, tab 251 has a side edge distance M1 (distance from side edge 255). Tab 252 has a side edge distance M2. Tab 253 has a side edge distance M3. Tab 254 has a side edge distance M4.

Figure 16:
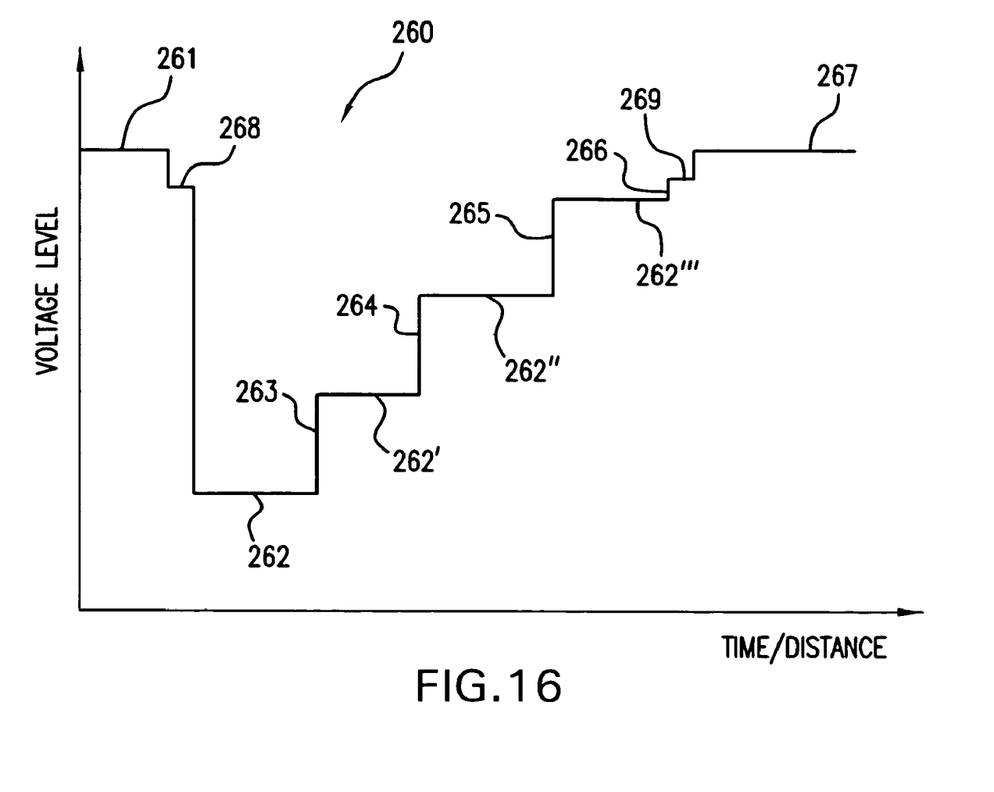
FIG. 16 is an exemplary two dimensional graph charting a change in voltage level caused by variously placed and sized tabs as the media sheet of FIG. 15 passes between the apparatus of FIG. 2, according to an embodiment of the present invention.

FIG. 16 is a two-dimensional graph 260 illustrating a measured voltage level as a media sheet 250 (FIG. 15) with four variously sized and located tabs pass through sensor 50 (FIG. 1). Initially, the measured voltage level is at a relatively high value 261. When a leading edge of the media sheet enters the calibration aperture 60, the measured voltage level drops to a lower value 268. When a leading edge of a media sheet 250 enters measurement aperture 62, the measured intensity level drops to a relatively low value 262. Voltage level change 263 corresponds to tab 251 (FIG. 15). Voltage level change 264 corresponds to tab 252 (FIG. 15). Voltage level change 265 corresponds to tab 253 (FIG. 15). Voltage level change 266 corresponds to tab 254 (FIG. 15). When the trailing edge of the media 250 enters the calibration aperture 60, the measured voltage level rises to a higher value 269. Once the trailing edge exits sensor 50 (FIG. 1), the measured intensity returns to a relatively high value 267.

Focusing on FIG. 16, voltage level change 263 has dimensions L1 and M1. M1 corresponds to the time between when the leading edge of the media sheet entered measurement aperture 62 and when voltage level change 263 reached its peak magnitude.

Figure 17:
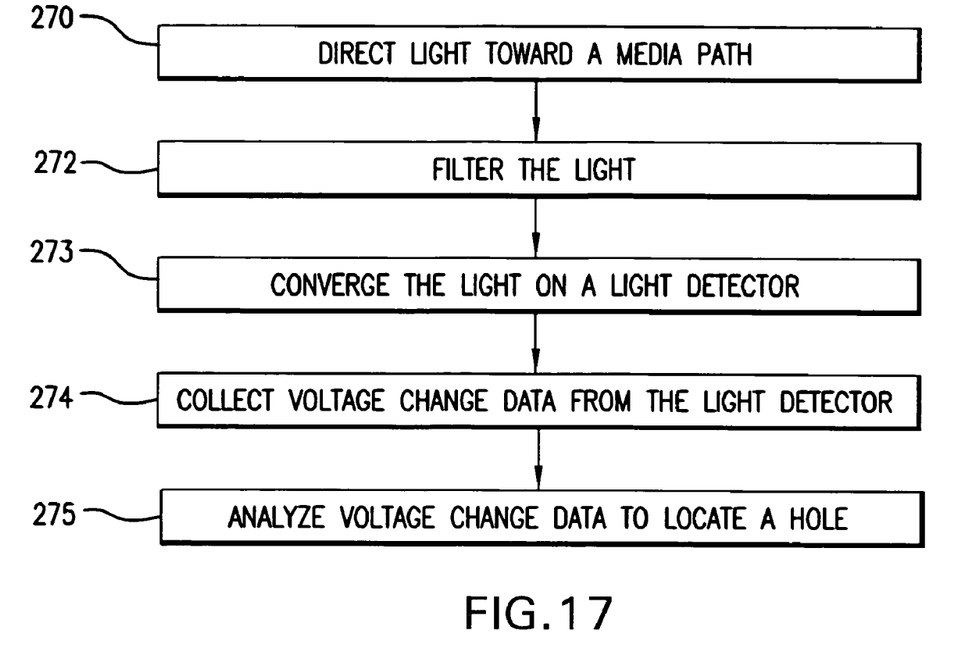
FIG. 17 is an exemplary flow diagram illustrating steps taken to locate a tab, according to an embodiment of the present invention.

Referring back to FIG. 15, side edge distance L1 can be calculated by a linear factor that depends primarily on the known size of calibration aperture 60 (FIG. 1) and the measured change in voltage level.

Where the velocity of media sheet 250 is known, L1 can be converted to a linear distances. Referring to FIG. 15, the size of tab 251 can be calculated as a function of L1 and M1. With respect to tabs 252-254, their sizes can be calculated in a similar fashion using L2-L4 and M2-M4, respectively Moving on, FIG. 17 is an exemplary flow diagram illustrating method steps for locating a tab. Light is directed toward a media path (step 270). The light is directed from a first side of a media path such that the light spans at least a portion of a width of the media path. The light is filtered (step 272). The light impinges upon a light detector (step 273). Voltage level change data is collected from the light detector (step 274). The voltage level change data collected corresponds to a voltage level change measured from a second side of the media path opposite the first side as print media is urged along the media path. The voltage level change data is analyzed to locate a hole (step 275).

Figure 18:
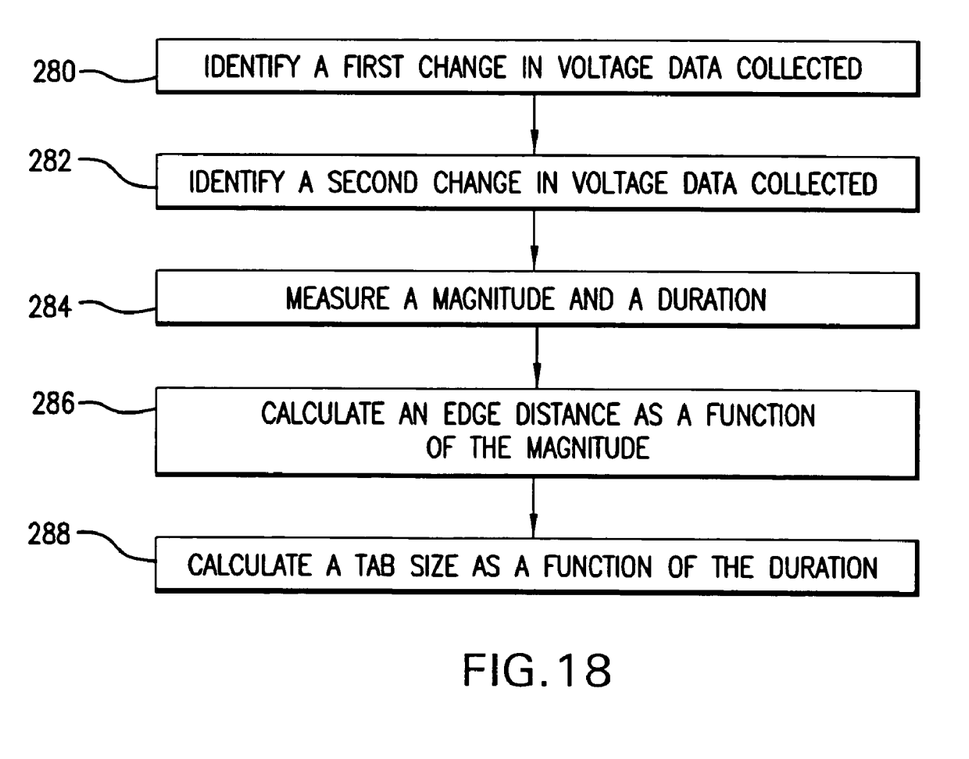
FIG. 18 is an exemplary flow diagram illustrating steps taken to identify a location and size of a tab based on a change in voltage level caused by that tab, according to an embodiment of the present invention

FIG. 18 is an exemplary flow diagram expanding on step 275. A first change in voltage data collected is noted (step 280). The first change, for example, may be a change from a relatively high value to a relatively low value indicating that the leading edge of a media sheet has been detected. A second change in the collected voltage level data is then noted (step 282). The second change, for example, may be an increase from the relatively low value to a value less than the relatively high value and then a return to the relatively low value. The magnitude of the second change and a duration of the second change at fifty percent of its magnitude are measured (step 284). An edge distance is calculated as a function of the measured magnitude (step 286). A magnitude is calculated as a function of the measured duration (step 208).

CONCLUSION: The illustrations of the Figures show the architecture, functionality, and operation of an exemplary environment in which various embodiments of the present invention may be implemented. Some of the Figures illustrate various embodiments of a sensor. The claimed subject matter is not limited to the embodiments shown. The sensor may be able to detect the change in voltage level as a result of the change in the intensity of a light directed across a portion of a width of a media path. The various block diagrams illustrate an example of the logical components that can be used to implement the various embodiments. Each block in the block diagrams may represent in whole or in part a module, segment, or portion of code that comprises one or more executable instructions to implement the specified logical function(s). Each block may represent a circuit or a number of interconnected circuits to implement the specified logical function(s).

Also, embodiments of the present invention can include any computer-readable medium for use by or in connection with an instruction execution system such as a computer/processor based system or an ASIC (Application Specific Integrated Circuit) or other system that can fetch or obtain the logic from computer-readable media and execute the instructions contained therein. "Computer-readable medium" can be any of one or more computer readable media that can contain, store, or maintain programs and data for use by or in connection with the instruction execution system. Computer readable media can comprise any one of many physical media such as, for example, electronic, magnetic, optical, electromagnetic, infrared, or semiconductor media. More specific examples of suitable computer-readable media include, but are not limited to, a portable magnetic computer diskette such as floppy diskettes or hard drives, a random access memory (RAM), a read-only memory (ROM), an erasable programmable read-only memory, or a portable compact disc.

Although the various flow diagrams show specific orders of execution, the orders of execution may differ from that which is depicted. For example, the order of execution of two or more blocks may be scrambled relative to the orders shown. Also, two or more blocks shown in succession may be executed concurrently or with partial concurrence. All such variations are within the scope of the claimed subject matter.

Embodiments of the present invention have been shown and described with reference to the foregoing exemplary embodiments. It is to be understood, however, that other forms, details, and embodiments may be made without departing from the spirit and scope of the invention which is defined in the following claims.

What is claimed is:

1. An apparatus for determining a media feature, comprising:
    a plurality of light filters such that the filters include a media measurement aperture and a calibration aperture and wherein the filters are spaced a predetermined distance apart to allow media to be introduced between the filters;
    a light source located substantially adjacent to one of the filters;
    a light detector located substantially adjacent to another of the filters;
    a processor; and
    evaluation logic for the processor configured to determine a size of a hole or a tab based upon output from the light detector.

2. The apparatus, as in claim 1, wherein the plurality of light filters are further comprised of:
    at least one calibration aperture; and
    at least one measurement aperture located substantially adjacent to the at least one calibration aperture.

3. The apparatus, as in claim 1, wherein the light source is further comprised of:
    a uniform light source.

4. The apparatus, as in claim 1, wherein the light source is further comprised of:
    an electroluminescent panel.

5. The apparatus, as in claim 1, wherein the light detector is further comprised of:
a photovoltaic cell.

6. The apparatus of claim 1, wherein the light source is configured such that light from the light source is concurrently transmitted through the media measurement aperture and the calibration aperture on one side of the media towards the light detector on another side of the media.

7. The apparatus of claim 1, wherein the light detector is configured to receive light from the light source that has passed by the media adjacent to at least two non-panel edges of the media.

8. A method for determining a media feature, comprising:
directing light toward a media path and a light detector;
filtering the light, wherein filtering comprises:
employing a calibration aperture; and
employing a measurement aperture located substantially adjacent to the calibration aperture;
collecting voltage change data from the light detector;
analyzing the voltage change data to determine the media feature, wherein analyzing comprises:
analyzing the voltage change data to identify a presence of a tab in the media, wherein the presence of the media in the media path blocks at least a portion of the light causing a first change in the voltage data collected;
wherein the presence of a tab in the print media causes a second change in the voltage data collected; and
wherein the analyzing further comprises:
measuring a magnitude and a duration corresponding to the second change;
ascertaining a suspected tab height corresponding to the magnitude;
ascertaining a width corresponding to the duration; and
comparing the suspected tab height to the width to determine if the second change represents a tab;
locating the calibration aperture in the media path so that it is always blocked by media;
measuring a translucence of the media;
locating the measurement aperture in the media path so that it interacts with the media; and
determining a feature of the media.

9. The method of claim 8, wherein the light is concurrently transmitted through the measurement aperture and the calibration aperture on one side of the media path towards the light detector on another side of the media path.

10. An apparatus comprising:
a computer readable medium having instructions for a method for determining a media feature, comprising:
directing light toward a media path and a light detector;
filtering the light, wherein filtering comprises:
employing a calibration aperture; and
employing a measurement aperture located substantially adjacent to the calibration aperture;
collecting voltage change data from the light detector; and
analyzing the voltage change data to determine the media feature, wherein analyzing comprises:
analyzing the voltage change data to identify a presence of a hole in the media, wherein the presence of the media in the media path blocks at least a portion of the light causing a first change in the voltage data collected;
wherein the presence of a hole in the print media causes a second change in the voltage data collected;
wherein analyzing comprises identifying the presence of the hole according to characteristics of the second change and wherein the analyzing further comprises:
measuring a magnitude and a duration corresponding to the second change;
ascertaining a suspected diameter corresponding to the magnitude;
ascertaining a width corresponding to the duration;
comparing the suspected diameter to the width to determine if the second change represents a hole;
locating the calibration aperture in the media path so that it is always blocked by media;
measuring a translucence of the media;
locating the measurement aperture in the media path so that it interacts with the media; and
determining a feature of the media.

11. The apparatus of claim 10, wherein measuring a duration comprises:
measuring a duration for which the second change remains equal to or greater than fifty percent of the magnitude, the method further comprising determining that the second change represents a hole when the comparison reveals that the width equals about eighty-six percent of the suspected diameter.

12. The media of claim 10, wherein the light is concurrently transmitted through the measurement aperture and the calibration aperture on one side of the media path towards the light detector on another side of the media path.

13. A method comprising:
directing light toward a media path and a light detector;
filtering the light;
collecting voltage change data from the light detector;
determining a size of a hole or a tab of the media based at least in part upon a magnitude of output from the light detector;
locating a calibration aperture in the media path so that it is always blocked by media; and
measuring a translucence of the media, wherein the size of the hole or the tab is based at least partially upon the measure translucence.

14. The method of claim 13, wherein the magnitude of output from the light detector comprises a magnitude of voltage from the light detector.

15. The method of claim 13, wherein the size of the hole of the tab of the media is based upon a predetermined relationship between the magnitude of the output from the light detector and the size of the hole of the tab.

16. The method of claim 15, wherein the predetermined relationship is contained in a lookup table contained in a processor-readable memory.

17. The method of claim 13, wherein the determining the size of a hole or a tab comprises determining the size of a tab.

18. The method of claim 17, wherein a height of the tab is determined based upon a change in the magnitude of the output from the light detector and wherein a width of the tab is determined based upon a duration of the change in the output from the light detector.

19. The method of claim 13, wherein the step of directing light toward the media path and a light detector is performed such that at least two non-parallel edges of the media block the light prior to the light that has passed by and adjacent to the at least two non-parallel edges of the media impinges the light detector.

20. An apparatus comprising:
a computer readable medium having instructions for a method for determining a media feature, comprising:
directing light toward a media path and a light detector;
filtering the light;
collecting voltage change data from the light detector; and analyzing the voltage change data to determine the media feature, wherein analyzing comprises:

analyzing the voltage change data to identify a presence of a hole in the media, wherein the presence of the media in the media path blocks at least a portion of the light causing a first change in the voltage data collected; wherein the presence of a hole in the print media causes a second change in the voltage data collected;

wherein analyzing comprises identifying the presence of the hole according to characteristics of the second change and wherein the analyzing further comprises:

measuring a magnitude and a duration corresponding to the second change;

ascertaining a suspected diameter corresponding to the magnitude;

ascertaining a width corresponding to the duration; and comparing the suspected diameter to the width to determine if the second change represents a hole, wherein measuring a duration comprises:

measuring a duration for which the second change remains equal to or greater than fifty percent of the magnitude, the method further comprising determining that the second change represents a hole when the comparison reveals that the width equals about eighty-six percent of the suspected diameter.

* * * * *